United States Patent [19]

Barach et al.

[11] 4,324,255
[45] Apr. 13, 1982

[54] METHOD AND APPARATUS FOR MEASURING MAGNETIC FIELDS AND ELECTRICAL CURRENTS IN BIOLOGICAL AND OTHER SYSTEMS

[76] Inventors: John P. Barach, 541 Hickory Trail Dr., Nashville, Tenn. 37209; John P. Wikswo, Jr., 1025 Manly La., Brentwood, Tenn. 37027

[21] Appl. No.: 128,197

[22] Filed: Mar. 7, 1980

[51] Int. Cl.³ .............................................. A61B 5/04
[52] U.S. Cl. .................................. 128/630; 128/653; 128/733; 324/117 R; 324/248
[58] Field of Search ............... 128/639, 653, 733, 630, 128/741; 324/127, 248, 117 R; 336/174, 175, 176, DIG. 1

[56] References Cited

U.S. PATENT DOCUMENTS

| | | | |
|---|---|---|---|
| 2,802,182 | 8/1957 | Godshalk et al. | 324/117 R |
| 2,836,791 | 5/1958 | Kaplan | 324/117 R X |
| 3,143,720 | 8/1964 | Rogers | 336/DIG. 1 X |
| 3,454,875 | 7/1969 | Bol et al. | 324/248 |
| 3,475,682 | 10/1969 | Peek et al. | 324/127 |
| 3,582,774 | 6/1971 | Forgacs | 324/127 X |
| 3,863,148 | 1/1975 | Fellrath et al. | 324/64 |
| 3,955,560 | 5/1976 | Stein et al. | |
| 3,957,036 | 5/1976 | Norman | |
| 3,980,076 | 9/1976 | Wikswo et al. | |
| 4,025,844 | 5/1977 | Deutscher | 324/248 |
| 4,031,882 | 6/1977 | DeLuca | |
| 4,046,141 | 9/1977 | DeLuca | |
| 4,079,730 | 3/1978 | Wikswo et al. | |

OTHER PUBLICATIONS

Wulfsohn et al., "The Nervous System and Electric Currents", Proc. of the Third Ann. Nat. Conf. of the Neuro-Electric Soc., New York-London, pp. 9–13, 1970.

*Primary Examiner*—Robert W. Michell
*Assistant Examiner*—John C. Hanley
*Attorney, Agent, or Firm*—Flehr, Hohbach, Test et al.

[57] ABSTRACT

A method and apparatus for measuring magnetic fields and electric current flow in biological systems and other systems employing a room temperature pick-up probe connected to a superconducting quantum interference device (SQUID).

2 Claims, 5 Drawing Figures

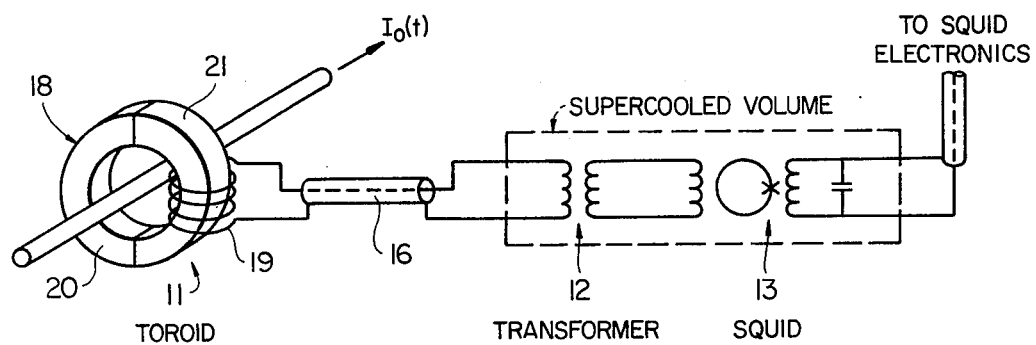
FIG_1
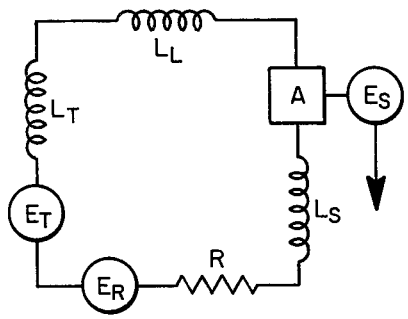
FIG_2
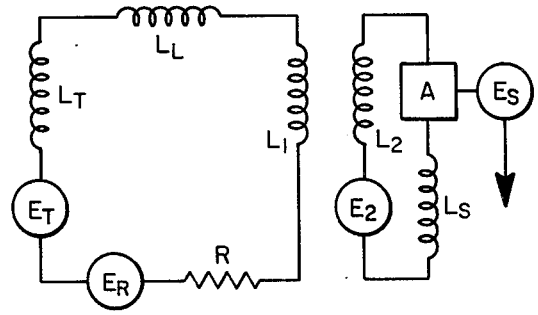
FIG_3
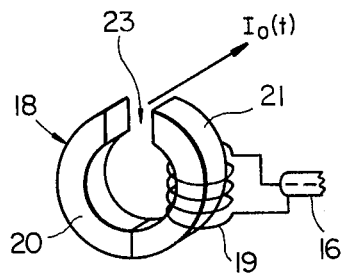
FIG_4
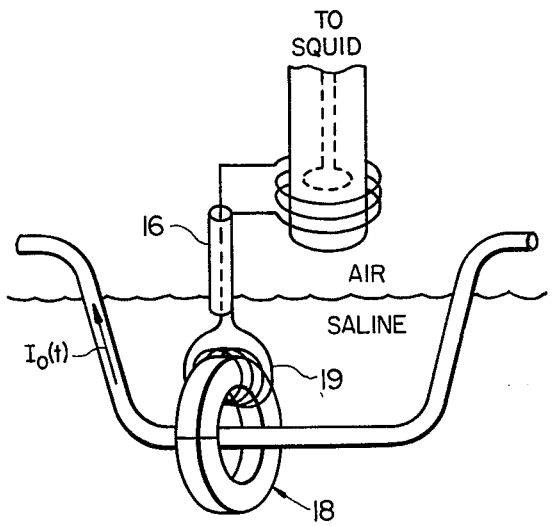
FIG_5

METHOD AND APPARATUS FOR MEASURING MAGNETIC FIELDS AND ELECTRICAL CURRENTS IN BIOLOGICAL AND OTHER SYSTEMS

This invention relates generally to a method for measuring electric currents produced in biological systems such as nerve and muscle fibers by measuring the magnetic field produced by such currents.

The prior art can be divided into three distinct areas: the measurement of biological magnetic fields, the direct measurement of the electric currents associated with nerve and muscle tissue, and the measurement of electric currents by measurement of their magnetic field.

Present day Superconducting Quantum Interference Device (SQUID) magnetic field detectors built for biomagnetic measurements are limited in that the magnetic field sensing coils have to be operated at cryogenic temperatures and as a result must be placed in an insulated vacuum enclosure such as a dewar. Because of the thickness of the dewar walls, the coils are at least one cm from the magnetic field source being studied. As long as the systems being studied are large as compared to one cm, this is not a serious limitation. However, typical nerve bundles, large single axons, and cardiac muscle fibers are approximately 0.5 mm in diameter, so that at a distance of one cm, the peak magnetic field from them is on the order of 1 picoTesla (pT). This field strength is barely at the level of detectability for a SQUID operating with a 1 kHz bandwidth. Furthermore, many details of the spatial variation of the magnetic field outside the nerve are not observable at distances greater than several nerve radii. While such a SQUID magnetometer can detect the magnetic field of an isolated frog sciatic nerve, its one cm coil-to-nerve separation, the intrinsic SQUID noise and environmental noise preclude any detailed or useful measurements.

These difficulties have been overcome by the present invention, which uses a small room temperature toroidal coil placed around the nerve, with the toroid connected to the SQUID. By detecting the magnetic field within one mm or less of the nerve surface rather than at one cm, a hundred-fold or larger increase in field strength can be obtained. The resulting combination of a room temperature toroidal coil and a superconducting magnetometer has sufficient spatial resolution and sensitivity to detect the 100 pT magnetic field of an isolated frog sciatic nerve with at least a forty-to-one signal to noise ratio (with signal averaging less than 1000 repetitive signals). If this measurement was attempted with a conventional SQUID magnetometer as used for measuring biomagnetic fields from the heart, the sensitivity of the SQUID magnetometer to external magnetic noise would require that the measurements be made in a magnetically quiet environment.

The present invention overcomes this limitation because the toroidal pickup coil is insensitive to magnetic field sources external to the toroid and it is possible to shield the SQUID sensor from magnetic noise and thereby utilize its full $6 \times 10^{-12}$ A/Hz$^{-\frac{1}{2}}$ sensitivity for measurements in a typical laboratory.

Furthermore, by using a toroid split into two semicircular halves, it is possible to clip the toroid around an exposed nerve or muscle fiber in vivo without requiring access to one end for threading through the toroid. Thus, this invention provides a means for measuring the magnetic field from electric currents as small as $10^{-8}$ Amps with a 500 Hz measuring bandwidth.

Much of the knowledge about the function of nerve and muscle cells has come from measurement of the electric fields that they produce when stimulated. However, it has proven difficult to measure electric current flow within these cells. It is possible to use voltage clamp techniques to measure transmembrane currents in large nerve axons, but a serious assumption must be made. These measurements of currents cannot be made during an action potential but must be measured when the transmembrane potential is held (clamped) at a particular fixed value. If has been assumed that the currents and membrane conductance are the same in the clamped state as during the action potential. In this invention, the internal currents are measured directly and can be determined during an action potential. If a transmembrane potential is measured simultaneously, it is also possible to compute the instantaneous membrane conductance. The voltage clamp technique per se cannot be applied to cardiac muscle, but the corresponding sucrose gap techniques for muscle often lead to ambiguous results. Also, muscle contraction following stimulation can break the microelectrodes.

The apparatus of the present invention is easier to use than a glass microelectrode. The toroid pickup coil and SQUID sensor combination of the present invention is significantly more sensitive than previously available current measuring devices and has the added advantage of not requiring puncture of the cell membrane. For example, it will be possible to monitor the function of nerves exposed during surgery without damage to or puncture of the nerve. The toroidal coil of the present invention can be surgically and permanently implanted around an intact human or animal nerve for monitoring the function of that nerve, either for diagnostic purposes or for controlling a prosthetic device. If the nerve is in fact a bundle of smaller nerve fibers, the magnetic measurement will be able to detect all of the fibers with more uniformity than could electric potential measurements on the outside of the nerve bundle.

Furthermore, the apparatus allows bioelectric signals to be monitored directly in the conducting fluid; unlike electrical signals, they are not shorted out by high conductivity fluid surrounding the nerve or muscle fiber. Nerves in air may produce millivolt potential differences along their surface. Immersed in a solution or medium with an electrical conductivity typical of living systems, a nerve will produce potentials on the membrane surface that are on the microvolt level. Thus, it is difficult to measure electrical signals of intact nerves. The magnetic method described by this invention functions when the nerve is immersed in conducting fluid, and is ideally suited for studying intact nerves in vivo. Equally important, this technique measures current density directly (properly it measures curl J but in simple axon geometries one uses Stokes' theorem at once) and allows determination of current profiles without assumptions about conductivity and electric boundary conditions that are necessary to unfold the nerve current from voltage recordings. Since the magnetic trace is very close to an actual current measurement, it is therefore a particularly strong complement to the electrical record.

Although the electrical potentials produced by a propagating nerve action potential have been measured, the accompanying magnetic fields have never been observed directly prior to this invention. The failure of previous attempts is readily understood. The nerve action potential has the form of a moving, azimuthally-symmetric solitary wave which can be modeled as two opposing current dipoles driven by a potential change on the order of 70 mV. The peak currents range from 5 to 10 μA. The external magnetic field B can be estimated using Ampere's law in which I is the net axial current enclosed by a closed path of integration c:

$$\oint_c \vec{B} \cdot \vec{dl} = \mu_0 I. \quad (1)$$

If the nerve is immersed in a conducting medium, the maximum magnetic field of 100 pT occurs at the nerve surface (r<0.3 mm for nerve bundles, r<<0.3 mm for single vertebrate nerves), with the particular detailed values depending upon the preparation used. The nerve is physically small and, moreover, the current distribution outside the nerve is largely quadrupolar so that the field falls off steeply with distance. Thus the magnetic field will decrease in proportion to $(r/R_n)^{-f}$ where r is the distance from the nerve, $R_n$ is the nerve radius, and $1 < f < 3$. As the distance from the nerve is increased, an increasing fraction of the external current returns within c, so that the field at 1 cm is a few pT and decreases thereafter in proportion to the inverse cube of the distance. The weakness of the magnetic field, its rapid falloff with distance, and the required 1 to 2 kHz bandwidth place the signal at the limit of detectability of magnetometers currently used for biomagnetic measurements.

Room temperature coils and conventional amplifiers have been used to obtain signals interpreted as the magnetic field from the action potential of an isolated frog sciatic nerve. These signals did not exhibit the expected reversal of polarity upon reversal of the direction of impulse propagation, which lead the investigators and others to question the validity of the results.

Because sciatic nerves produce readily measured potentials only if the nerve is in air, these investigators attempted to measure the magnetic field of a nerve supported in air. As a result, all of the electrical currents were confined to the nerve bundle and the coaxial layer of moist electrolyte surrounding it. As a consequence, there was no magnetic field in the air outside such a nerve. The previous attempts could not have detected a magnetic field and did not. These previous measurements were also sensitive to capacitative coupling, since three electrostatically-shielded pickup coils of adequate sensitivity were unable to detect the magnetic field of a moist nerve in air.

This invention avoids these difficulties by using a nerve naturally immersed in a natural, conducting medium.

The apparatus of the present invention has several major advantages over previous magnetic devices to measure weak electric currents. The most important is its high sensitivity to currents threading the toroid and low sensitivity to external currents and their magnetic fields. Prior art devices that utilize toroidal pickup coils to measure currents have all used conventional vacuum-tube or semiconductor amplifiers to measure the voltages induced in the pickup coil. For a fixed amount of current passing down a wire or nerve threading a toroid, the signal-to-noise ratio is determined by the effective radius of the toroid, the number of turns in the coil, the Johnson noise in the coil and the amplifier noise. There are several design criteria that result in compromising tradeoffs. First, the toroid dimensions should be small to allow coupling to the large magnetic field close to the surface of the nerve or wire. Secondly, conventional vacuum tube or semiconductor amplifiers are optimized for measuring voltages across sources with a high resistance. The impedance matching criteria can in theory be met by utilizing a large number of turns of wire in the coil, but as the number of turns increases, so must the size of the toroid. Decreasing the wire size to allow small toroids results in a corresponding increase in coil resistance. Furthermore, a large number of turns introduces significant capacitance, which combines with the necessarily large inductance of the detector to form an LC resonant circuit with extremely limited band-pass and impulse response characteristics. As a result, it is difficult to build a toroid/conventional amplifier system capable of detecting currents smaller than $10^{-6}$ amps in the bandwidth of 1 Hz to 2 Khz. These limitations are overcome by the present invention, since the SQUID is optimal for measuring currents from sources with a large inductance and a low resistance. Thus toroids can be constructed with only a small number of turns, thereby minimizing the resistance of the coil with its associated Johnson noise and allowing construction of extremely small toroids of high sensitivity.

It is an object of this invention to provide an improved method and apparatus for measuring the magnetic fields and electric currents in nerves, muscles, and other electrical systems.

It is another object of this invention to provide a method for determining the instantaneous conductance of a nerve membrane.

It is a further object of this invention to provide a method for determining the internal currents in nerve and muscle cells.

It is another object of this invention to provide an apparatus for measuring the magnetic fields of biological systems.

It is another object of this invention to provide an improved, compact apparatus for measuring weak electric current flow in wires and microcircuits.

The foregoing and other objects of the invention are achieved by an apparatus including a supercooled vacuum enclosure containing a SQUID sensor and a room temperature toroidal pick-up coil connected to the SQUID sensor.

FIG. 1 is a schematic diagram showing an apparatus in accordance with the present invention including a toroidal pick-up probe surrounding a nerve or wire carrying a current $I_o(t)$.

FIG. 2 is an equivalent circuit of a toroidal pick-up coil connected directly to a SQUID.

FIG. 3 is an equivalent circuit similar to FIG. 2 with a transformer having primary inductance $L_1$ and secondary inductance $L_2$ connected between the pick-up coil and the SQUID.

FIG. 4 is a schematic diagram of a toroidal pick-up probe including a gap in the toroidal core for detecting adjacent currents.

FIG. 5 is a schematic diagram of the apparatus used in measurements already completed, with a nerve and pick-up core immersed in a conductive solution.

The apparatus of the present invention has three main parts as shown in FIG. 1: the toroidal probe 11, an impedance matching transformer 12 (optional), and the SQUID sensor 13. The supercooled environment required for the operation of the SQUID can be provided by a small cryogenic dip-probe to house the SQUID sensor and to allow its operation in a liquid helium storage dewar flask. The dip-probe consists of a ½ inch diameter metal tube approximately 1 m long with the SQUID located in a super-conducting lead shield at the bottom, connected to a junction box at the top via two small coaxial cables. One of these cables connects the SQUID sensor to the SQUID electronics, the other connects the SQUID to the toroidal pick-up probe 11. The dip-probe also contains a liquid helium level detector to allow determination of the storage dewar helium volume without removing the probe. Depending upon the inductance of the toroid coil and the SQUID sensor, an impedance matching network or transformer 12 may be added between the toroidal probe and the SQUID. The toroidal probe is operated at ambient temperature and thus is not superconducting. The probe is connected to the impedance matching network by a coaxial cable 16 to prevent currents from being induced by stray magnetic fields. All or part of the impedance matching network can be operated in the superconducting state at cryogenic temperatures to utilize the absence of electrical resistance and the associated Johnson noise. If the impedance matching transformer is not used, the coaxial cable can be connected directly to the SQUID. In either case, care must be taken to prevent coupling radio frequency interference to tne SQUID. The toroidal probe includes a core 18 with a winding 19. Ferrite toroids with a 2.6 mm diameter may be used for the core, which supports the pickup coils 19. By using molypermalloy toroids, higher permeabilities can be achieved, allowing the use of fewer turns without an increase in the effects of stray inductance. Fabrication of the molypermalloy cores is straightforward and only requires careful annealing prior to their use. By fabricating cores split into two halves 20 and 21, it is possible to make pickup coils that can be clipped around nerves, muscles, and other systems carrying electrical current without damage or interruption of the system or the current it carries. If desired, the entire core can be covered with a grounded electrostatic shield or an insulating layer (not shown).

The equivalent circuit of a toroid connected directly to a SQUID current sensor is shown schematically in FIG. 2. The toroid is represented by a voltage source $E_T$ that corresponds to the emf induced in the toroid by the time varying currents $I_o(t)$, FIG. 1, threading it, by an inductance $L_T$, and by a resistor R. The resistor has a Johnson noise voltage $E_R$ associated with it. The leads connecting the toroid to the SQUID have an inductance $L_L$; the resistance of the leads is assumed to be contained in R. The SQUID is treated as a perfect ammeter A with an inductance $L_S$. The intrinsic noise of the SQUID and its electronics are indicated by the voltage source $E_S$. For this analysis, we will assume that the SQUID noise appears only on the output of the SQUID and does not reflect back into the input circuit.

The voltage induced in the toroid by a current $I_o \sin(\omega t)$ threading the toroid can be determined by using Ampere's law to compute the flux linking the coil and Faraday's law to obtain the amplitude $E_T$ of the sinusoidal electromotive force given by $$E_T = I_o N \omega t (\mu \mu_o / 2\pi) \ln(r_1/r_2) = L_T \omega I_o / N. \tag{2}$$

where N is the number of turns in the toroidal coil 19, $\mu_o$ is the permeability of free space, $\mu$ is the relative permeability of the toroid core, t is its thickness and $r_1$ and $r_2$ are the inner and outer radii of the toroid. The inductance of the toroid is $L_T$. The magnitude $I_1$ of the current induced in the circuit by the sinusoidal voltage $E_T$ is determined by the impedance $Z_1$ of the entire circuit $$I_1 = E_T/Z_1 = (E_T/R)[1 + (L_{E1}\omega/R)^2]^{-\frac{1}{2}}, \tag{3}$$

where the inductance $L_{E1}$ is $$L_{E1} = L_T + L_L + L_S \tag{4}$$

Equation (3) shows that the circuit acts as a low-pass filter with the half-power point occuring where $\omega L_{E1}/R = 1$. However, the voltage induced in the circuit by the toroid, as given by Eq. (2), is proportional to $\omega$ so Eq. (3) can be written as $$I_1 = (I_o/N)(L_T/L_{E1})[R/L_{E1}\omega)^2 + 1]^{-\frac{1}{2}} \tag{5}$$

This indicates that the entire circuit behaves as a high-pass filter for currents $I_o \sin(\omega t)$ threading the toroid, with the half-power point at $\omega L_{E1}/R = 1$. At frequencies well above the half-power point, the last term on the right approaches unity. In this limit, the current induced in the circuit is proportional to 1/N times the current threading the toroid: the circuit serves as a 1:N step-down current transformer so that less current is induced in the circuit than threads the toroid. Since the SQUID is a current sensing device rather than a voltage sensing one, it is important to maximize the current measured by the SQUID by minimizing the number of turns on the toroid. The practical limit of this occurs when the inductance of the coil coupling to the ferrite core approaches the stray inductance of the circuit.

Given this description of the system response to current threading the toroid, we can add the effects of noise to estimate the signal-to-noise ratio of the system. The Johnson noise from the resistor can be described in terms of a spectral power density.

$$<E_R^2> = 4kTR \tag{6}$$

where T is the absolute temperature and k is Boltzman's constant. The LR circuit acts as a low-pass filter on this voltage, so that the spectral power density of the noise currents is given by $$<i_R^2> = (4kT/R)[1 + (L_{E1}\omega/R)^2]^{-1} \tag{7}$$

This implies that the SQUID will detect signals preferentially at frequencies above $\omega = R/L_{E1}$ and detect the Johnson noise preferentially below that frequency. The effects of the noise is the output can be further reduced without affecting the signal by limiting the output bandwidth of the SQUID to frequencies above $\omega = R/L_{E1}$.

The intrinsic SQUID noise can be conveniently described in terms of an effective noise power density $<i_S^2>$ at the input. Typically, input noise current densities as low as $6 \times 10^{-12}$ A$\text{Hz}^{-\frac{1}{2}}$ can be obtained at 1 kHz. The total RMS noise current $I_N$ in a measuring bandwidth $\omega_1 < \omega < \omega_2$ is thus $$I_N = \left[ \int_{\omega_1}^{\omega_2} (<i_S^2> + <i_R^2>) d\omega \right]^{\frac{1}{2}}, \tag{8}$$

If we assume that the SQUID current noise is white in the frequency range of interest, and that the Johnson current noise is given by Eq. (7), then Eq. (8) can be integrated to yield $$I_N = \{<i_S^2>(\omega_2-\omega_1)+\omega_o(4kT/L_{E1})[\arctan(\omega_2/\omega_o)-\arctan(\omega_1/\omega_o)]\}^{\frac{1}{2}}. \quad (9)$$

with the toroid cut-off frequency $\omega_o$ equal to $R/L_{E1}$.

Equations (5) and (9) can be combined to estimate the ultimate sensitivity of a toroidal coil to current threading it. The minimum detectable current $(I_o)_{min}$ can be defined as the value of $I_o$ in Eq. (5) for which $I_1$ equals $I_N$ in Eq. (9), i.e.

$$(I_o)_{min} = NI_N(L_{E1}/L_T)[(\omega_o/\omega)^2+1]^{\frac{1}{2}} \quad (10)$$

This equation suggests the complexity of optimizing the system parameters. For example, decreasing N will improve the sensitivity, but will decrease R, which is some linear function of N and also decrease $L_T$, which is a quadradic function of N, thereby shifting the cut-off frequency $\omega_o$. This equation also provides the motivation for the high permeability core: it provides a large inductance with few turns, which is crucial for high sensitivity and wide bandwidth.

To elucidate the nature of the dependence of $(I_o)_{min}$ on experimental parameters, consider a case in which the bandpass is from $\omega_1=\omega_o/2$ to $\omega_2=2\omega_o$, with $\omega_o=R/L_{E1}$. Further, let us require that $L_T$ be large enough that it dominates $L_{E1}$. Then $$(I_o)_{min} = N\sqrt{\omega_o}\{[(\omega_o/\omega)^2+1][1.5<i_S^2>+2.5kT/R-]\}^{\frac{1}{2}}. \quad (11)$$

This equation shows that the best sensitivity occurs at the higher frequencies from $\omega=\omega_o$ to $2\omega_o$. To the extent that $L_T \approx AN^2$ and that $R \approx BN$, where A and B are constants, $\omega_o=(B/A)(1/N)$ and $(I_o)_{min}$ rises as $\sqrt{N}$ so that the minimum turn number is indeed desired.

A typical toroid has a 1.3 mm mean radius, a 1.2 mm thickness, and a $\mu/\mu_o$ of 6800, for an $L_T$ of 27 $\mu$H and an R of 0.1$\Omega$, giving a cut-off frequency of $\omega_o=590$ Hz. The RMS current noise $I_N$ in a 500 to 1500 Hz bandwidth is given by Eq. (9) and is $1.2\times10^{-7}$ A, with the Johnson noise power a factor of $10^5$ greater than that for the SQUID noise. With this 1000 Hz measuring bandwidth, a 1000 Hz sinusoidal current of $6.1\times10^{-7}$ A can be detected by the toroid with a unity signal-to-noise ratio. This represents at least a three order of magnitude increase in sensitivity compared to commercially available current probes. As we will now show, further improvements in sensitivity can be realized by using an impedance matching transformer.

If a superconducting impedance matching transformer is added, the equivalent circuit can be modified as shown in FIG. 3 to include separate primary and secondary circuits connected only by an electromotive force $E_2$ in the secondary due to currents in the primary. Since we will assume the secondary to be super-conducting, it has no resistance and thus it has a flat frequency response. The effective inductance of the primary circuit will be $$L_{E1} = L_T + L_L + L_1\left[1 - \frac{k^2L_2}{L_2+L_S}\right], \quad (12)$$

where $L_1$ and $L_2$ are the transformer inductances on the toroid and SQUID sides of the transformer, respectively, and k is the transformer coupling constant which is equal to the mutual inductance M divided by $(L_1L_2)^{\frac{1}{2}}$. The second term in the brackets accounts for the loading of the primary circuit by the secondary. Similarly, the effective inductance $L_{E2}$ of the secondary circuit will be $$L_{E2} = L_S + L_2\left[1 - \frac{k^2L_1}{L_1+L_T+L_L}\right]. \quad (13)$$

The current induced in the primary is given by Eq. (3). The voltage $E_2$ induced in the secondary is $$E_2 = M(dI_1/dt) = L_{E2}(dI_2/dt) \quad (14)$$

The current induced in the secondary is $$I_2 = I_1M/L_{E2} = (I_o/N)(L_T/L_{E1})(M/L_{E2})[(R/L_{E1}\omega)^2+1]^{-\frac{1}{2}} \quad (15)$$

The minimum detectable signal is given by Eq. (10) with an additional multiplicative factor of $(L_{E2}/M)$, and the RMS noise current is given by Eq. (9) with a factor of $(M/L_{E2})$ multiplying the second term in the braces. For the same SQUID and toroid inductances used previously, a transformer with a primary inductance $L_1$ of 45 $\mu$H, a secondary inductance $L_2$ of 3.3 $\mu$H, and a coupling coefficient of 0.8 will provide a minimum detectable current at 1000 Hz of $2.2\times10^{-8}$ A in a 500 to 1000 Hz bandwidth, a factor of five improvement over the unmatched case. Further improvements should be possible by optimizing toroid and SQUID parameters.

The response of the toroid-SQUID system in FIGS. 2 and 3 to a time-varying current threading the toroid is given by the differential equation describing the current induced in the primary circuit $$L_{E1}(d/dt)[I_S(t)]+I_S(t)R=E_T(t)=(L_T/N)(d/dt)[I_o(t)] \quad (16)$$

which can be integrated to yield $$I_o(t) = \frac{L_{E1}}{L_T}I_1(t) + N\frac{R}{L_T}\int_0^t I_1(t')dt'. \quad (17)$$

The second term on the right side of this expression represents the correction that must be applied to the signal to account for the low-frequency cut-off of the resistive pick-up coil.

There are several adaptations of this preferred embodiment that greatly extend the utility of this invention. By immersing the toroid in a conducting medium, it is possible to map out the electric current distribution in that medium. By rotating the toroid about an axis through a major diameter, it is possible to measure the steady current distribution as well as the time-varying one. If the coil form, either in the form of a toroid or another shape, has a section of its circumference with low magnetic permeability in contrast to the remainder of the form with high permeability, possibly as the gap 23 provided in the core 18, FIG. 4, it will become sensitive to currents flowing adjacent to the low-permeability section but not necessarily threading the form. While this will increase the sensitivity to external fields, this modification will greatly increase the flexibility of the method in that the coil could be brought up adjacent to a nerve that has been exposed.

In summary, this invention provides a means for measuring weak electrical currents in biological and other electrical systems by using a toroidal probe that detects the magnetic field produced by the time-varying electric current passing through the center of the toroid. If a wire or an electrically active biological preparation is threaded through the toroid, the device can measure the net current being conducted along the wire or preparation. If a split toroid is used, the device can be placed around the wire or biological preparation without requiring access to one end for threading through the toroid. For example, it will be possible to use this device to monitor the functional integrity of an in vivo human nerve bundle during surgery without damage to or puncture of the nerve bundle once it has been exposed.

While the apparatus measures the magnetic field linking the ferrite core, Ampere's law provides a one-to-one correspondence between that field and the net current threading the toroid. Thus the system is the first to provide direct, quantitative interpretation of biomagnetic signals in terms of their bioelectric current densities. In the case of a single nerve axon, the current density within the nerve axoplasm is several orders of magnitude larger than that immediately outside the nerve. If a small toroid is placed around such a nerve immersed in a conducting medium, the net current linking the toroid will primarily be due to intracellular currents; most extracellular currents will flow outside the toroid. For this reason, the system provides a technique for measuring intracellular current densities without puncturing the cell membrane. This technique allows determination of current profiles without the assumptions regarding conductivity and electric boundary conditions that are required to determine intracellular currents from extracellular voltage recordings. When combined with transmembrane potential measurements, this invention provides a method for direct measurement of transmembrane conductance during an action potential.

In one example, sciatic nerves from bullfrogs (*Rana catesbeiana*) were dissected and placed in a dish containing aerated Ringer's (saline) solution, FIG. 5. The magnetic fields were recorded with a SHE Model BMP-55 SQUID magnetometer ($1.3 \times 10^{-14}$ T(Hz)$^{-\frac{1}{2}}$ sensitivity, 18.7 mV per flux quantum calibration). The SQUID magnetometer utilizes a Superconducting Quantum Interference Device to detect magnetic flux changes through a superconducting pick-up coil in a liquid helium environment. At the closest coil-to-nerve separation of 15 mm, the nerve magnetic field could barely be detected.

Considerable effort was thereby expended to increase the signal-to-noise ratio. The distance between the nerve and the detector coil was reduced an order of magnitude by threading the nerve through a toroidal probe in accordance with the invention. The probe consisted of four turns of No. 38 wire wound on a 1.2 mm thick ferrite core of minor diameter 1.2 mm, major diameter 2.6 mm, and effective relative permeability at 2000 Hz of 6800. The effective cross sectional area of this toroidal pick-up coil was $3.9 \times 10^{-2}$ m$^2$. The toroid was inductively coupled (mutual inductance 5.4 nH) to the magnetometer face coil via a transfer coil wrapped around the outside of the dewar. The signals induced in the nerves were detected and analyzed.

This invention represents the first SQUID magnetometer utilizing a miniature, room temperature pickup coil. While the Johnson noise associated with such a resistive coil may prove disadvantageous in other applications, the filter-like behavior of the LR circuit that comprises the pickup coil minimizes or eliminates this problem for this application. Because the SQUID is optimized for measuring currents from high inductance, low resistance sources, the application of a SQUID instead of conventional amplifiers provides for a substantial increase in sensitivity over that which can be obtained using previously available devices.

What is claimed is:

1. The method of measuring the electric currents in an nerve, muscle fiber, biological system or organ which comprises the steps of coupling at room temperature a toroidal core to the magnetic fields induced by said currents, sensing the magnetic fields coupled into said toroidal core and generating an output current, and measuring the output current with a superconducting quantum interference device (SQUID).

2. The method of measuring the electric currents in an intact nerve, muscle fiber, biological system or organ which comprises the steps of immersing the nerve, muscle fiber, biological system or organ in a conducting medium such as saline, biological media or tissue, coupling at room temperature a toroidal core immersed in the conducting media to the magnetic fields induced by said currents, sensing the magnetic fields induced by said currents coupled to said toroidal core and providing an output current, and measuring the output current with a superconducting quantum interference device (SQUID).

* * * * *